United States Patent [19]

Simms

[11] Patent Number: 4,585,437
[45] Date of Patent: Apr. 29, 1986

[54] INTRODUCER FOR AN UMBILICAL ARTERY CATHETER

[76] Inventor: Mark D. Simms, 18 Tamarack La., Woodbury, Conn. 06798

[21] Appl. No.: 632,644

[22] Filed: Jul. 20, 1984

Related U.S. Application Data

[63] Continuation-in-part of Ser. No. 463,143, Mar. 17, 1983, abandoned, which is a continuation-in-part of Ser. No. 225,766, Jan. 16, 1981, abandoned.

[51] Int. Cl.⁴ ............................................. A61M 29/00
[52] U.S. Cl. ..................................... 604/106; 604/264; 128/345
[58] Field of Search ................... 128/303 R, 341, 343, 128/345, 17-19, 342; 604/105-109, 264, 164, 171, 158, 160, 161, 162, 166

[56] References Cited

U.S. PATENT DOCUMENTS

| | | | |
|---|---|---|---|
| 380,745 | 4/1888 | Chamberlin | 128/3 |
| 668,879 | 2/1901 | Miller | 128/343 |
| 762,743 | 6/1904 | McDade | 128/17 |
| 1,412,975 | 4/1922 | Stanton | 604/108 |
| 1,538,678 | 5/1925 | Blinn | 604/59 |
| 1,538,679 | 5/1925 | Blinn | 604/59 |
| 3,169,529 | 2/1965 | Koenig | 128/345 X |
| 3,224,437 | 12/1965 | Hardgrove | 128/9 |
| 3,698,387 | 10/1972 | Moore et al. | 128/9 |
| 3,877,429 | 4/1975 | Rasumoff | 128/345 X |

FOREIGN PATENT DOCUMENTS

| | | | |
|---|---|---|---|
| 299246 | 10/1928 | United Kingdom | 128/9 |
| 2031733 | 4/1980 | United Kingdom | 604/171 |

Primary Examiner—Michael H. Thaler
Attorney, Agent, or Firm—Walter G. Finch

[57] ABSTRACT

The invention is an improved device for introducing an umbilical artery catheter into an infant. Difficulty is experienced in introducing a catheter into the arterial system of an infant through the umbilical stump of a new born baby. The use of forceps to aid in the introduction often tears the arterial system and adds to the problem. The introduction of the catheter is particularly difficult in premature infants. The device consists of a funnel-like body with a handle-like member at the enlarged open end. At the end inserted into the arterial system, the small end of the funnel-like body consists of a plurality of prong-like nibs. The small end at the distal end of the prong-like nibs is bulbous-like and serves to prevent the device from being exuded from the arterial system once it is in place.

10 Claims, 7 Drawing Figures

INTRODUCER FOR AN UMBILICAL ARTERY CATHETER

This patent application is a continuation-in-part of my U.S. patent application Ser. No. 06/463,143 filed Mar. 17, 1983 for "Introducer For An Umbilical Artery Catheter", abandoned, which was a continuation of U.S. patent application Ser. No. 225,766 filed Jan. 16, 1981 for "Introducer For An Umbilical Artery Catheter", abandoned.

BACKGROUND AND SUMMARY OF THE INVENTION

The invention relates to medical devices, and in particular to devices, means, or systems used in cardiovascular studies, treatments, or investigations. Specifically, the invention relates to devices used for blood studies of infants.

A need has existed for an improved means and method for sampling and monitoring the blood system of infants, and more particularly premature infants. This present invention provides a device to improve the existing means and methods.

In new born infants, particularly infants born prematurely, there is often a problem with lungs that do not inflate properly. As a result, the baby does not get enough oxygen for proper life support. This premature lung syndrome in premature infants is called Hyaline Membrane Disease.

While sampling and monitoring the blood system infants that are born at term may encounter the same problems, the need for such sampling and monitoring is usually not required. The present invention may be used on term infants as well as on premature infants.

The sampling and monitoring of the blood in new born infants is performed by inserting a catheter into the umbilical artery at the umbilical stump (the shortest section of the umbilical cord that remains at the infant's body after the surgical procedure at birth).

One of the two umbilical arteries in the umbilical stump is used for the blood sampling and monitoring in new born infants. The sampling and monitoring is performed by passing a catheter into one of the umbilical arteries.

Inserting the catheter into the artery is difficult. The two umbilical arteries and an umbilical vein in the umbilical stump are surrounded by, and more or less held in place, by Wharton's Jelly, a jelly-like substance. The jelly-like substance really provides no firm support to the umbilical arteries, particularly in regard to the need for support as hereinafter described in conjunction with the insertion of the aforementioned catheter.

The insertion of the catheter in an umbilical artery in the umbilical stump, in order to sample and monitor the blood, is usually done during the first three or four days of the baby's life, during which the need for critical information is important to the physician.

The umbilical stump extends or sticks up about one-half an inch above the abdomen. The catheter must be inserted a sufficient distance into the umbilical artery so that it is beyond the skin, past the sphincter-like muscle under the skin. The umbilical arteries go to the aorta at the heart and is the means for obtaining a central arterial blood sample to read arterial oxygen content or tension either intermittently or on a continuous second to second basis. The catheter may also be used to take a blood sample for analyzing various other medical determinations.

During the period of Hyaline Membrane Disease, the infant may be connected to a respirator or may be given supplementary oxygen if not enough is supplied by the lungs, in order to avoid brain damage. Time is important for the infant's safety in order to avoid the danger of brain damage. Thus, the monitoring of the blood sample is very important at the early stages just after birth. The faster the catheter can be put into the umbilical artery for the monitoring process, the better for the infant.

If too much oxygen is supplied, there may be a risk of retrolental fibroplasia (blindness). Thus, a further factor in the importance of a need for an easy and quick means of inserting the catheter for monitoring purposes.

When the catheter is inserted in the umbilical artery, it is difficult, and any relative inexperience by the person inserting it can increase the difficulty. As there is no support in the aforementioned jelly-like substance, the artery end can be pushed down into the unsupportive jelly-like substance during the attempt to insert the catheter.

The prior art method is to use forceps to open or stretch apart the open entrance to the umbilical artery and hold it open, in a somewhat elliptical or rather flat elliptical configuration. Inserting the catheter into this unreceptive opening is difficult. Often the forceps will cut or tear pieces out of the edge of the artery, or as mentioned hereinbefore, the artery end gets pushed down into the jelly-like substance.

In the present invention, a funnel-like device, having the smaller or exit end taper to a diameter less than the inside diameter of the umbilical artery, is first inserted into the end of the umbilical artery at the surgically severed surface of the umbilical cord which then leaves the umbilical stump.

The funnel-like device has the tapered smaller or exit end formed into a plurality of sping-like prongs which will expand or move outwardly as the catheter is inserted and permit it to pass through. Thus, initially the tapered end is very small to permit insertion into the umbilical artery, but is expandable to permit the larger catheter to pass through and into the umbilical artery.

Funnel-like devices have been used in the prior art for guiding tools and other items in a specific direction, but were not of a structure that permitted an expanded configuration. However, there is a special problem with merely inserting such a funnel-like means into an artery-type interior, the artery has a tendency to exude the item being inserted as another item is passed through it.

When inserting a funnel-like device into an artery, as described hereinbefore, and then passing a catheter through it, the smooth muscle of the artery contracts around the catheter and concurrently squeezes or exudes an ordinary encircling ring, such as the funnel-like end, out of the artery.

To overcome this exuding action the present invention is bulbous-like on the end. Thus, as the smooth muscle artery contracts and closes and squeezes around the cathether it also contracts and closes and squeezes around the end of the funnel-like device. However, the bulbous-like end permits the contraction to close around the top and over the bulbous end, thus preventing it from being exuded from the artery. A novel and unique feature in the present invention.

As the lead tips under the bulbous end and then the bulbous end is inserted into an artery the device may be held with a forceps above the bulbous end, an additional advantage of the novel and unique device, until the catheter is inserted. The bulbous end may normally be inserted approximate one-quarter inch below the surface of the umbilical stump, sufficient to prevent being exuded.

After the catheter is in place the introducer, the funnel-like device, may be left in place, slipped out of the artery and partially up the catheter, or it may be cut off for disposal.

With care afforded by the facility of the catheter monitoring system introduced by the present invention, the lung problem usually is resolved in the first three or four days of the infant's life and the catheter is removed. This also guards against infection if longer periods were used. The catheters may range up to approximately one-eighth inch in diameter.

The plurality of prong-like ends may be formed by mere slits or by a keyhole-like separation.

It is, therefore, an object of the invention to provide a device for introducing a catheter into an artery that may be used on new born infants.

It is another object of the invention to provide a device for introducing a catheter into an artery that is funnel-like in configuration to receive and guide a catheter.

It is also an object of the invention to provide a device for introducing a catheter into an artery that has a plurality of prong-like nibs at the end that may be expanded outwardly as an object passes therethrough.

It is yet another object of the invention to provide a device for introducing a catheter into an artery that has a bulbous end on a plurality of prong-like nibs to provide a means for preventing a smooth muscle artery from exuding the device.

Further objects and advantages of the invention will become more apparent in the light of the following description of the preferred embodiments.

DESCRIPTION OF THE PREFERRED EMBODIMENTS

Figure 1:
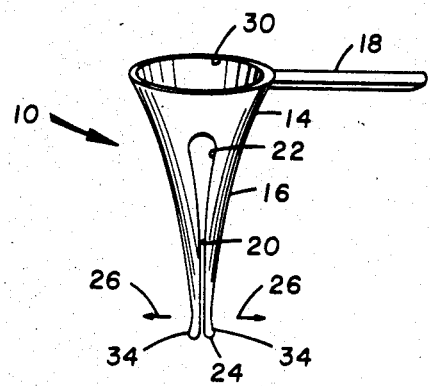
FIG. 1 is a pictorial view of an introducer for guiding a catheter into an artery.
Figure 2:
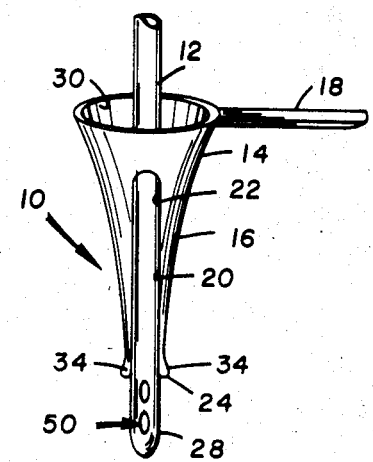
FIG. 2 is a pictorial view of an introducer with an end of a catheter therethrough.
Figure 4:
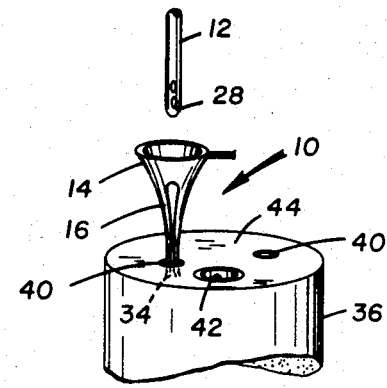
FIG. 4 is a pictorial view of an introducer inserted into an artery in an umbilical stump with a partial view of a catheter poised for insertion.

Referring to the drawings and particularly to FIGS. 1, 2, and 4, an introducer for an umbilical catheter is shown at 10.

The introducer 10 for umbilical catheter 12 consists of a funnel-like upper body portion 14, a plurality of nibs 16, and a handle or holding means 18.

Figure 3:
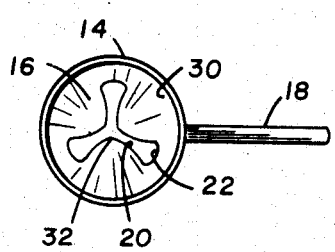
FIG. 3 is a top view of FIG. 1.

The funnel-like upper body portion 14 transversely may be configured generally as a circular and conical-like body, tapered square body, or any other geometrical configuration to form a tapered passageway 30 therethrough. In FIG. 3 the transverse configuration is shown circular, which is a preferred embodiment for a conical-like configuration.

The plurality of nibs 16 extend downwardly from the tapered sides of the funnel-like upper body portion 14 and are contiguous therewith. In fabrication the nibs 16 may be monolithic with the funnel-like upper body portion 14 or may be separately affixed thereto. The monolithic configuration is a preferred embodiment.

In the plurality of nibs 16 shown in FIGS. 1, 2, 3, and 4, FIG. 3 illustrates three nibs. It is to be understood, however, that any plurality of nibs may be used for the purpose as hereinafter described.

The plurality of nibs 16 may be formed by a plurality of slits 20 in the nib portion of a monolithically formed introducer 10. To provide greater flexibility to the plurality of nibs 16 a keyhole-type opening or reversed tear-drop type opening 22 may be provided at the uppermost portion of each of the plurality of slits 20 where each of plurality of nibs 16 joins and is contiguous with the funnel-like upper body portion 14.

The plurality of nibs 16 are each flexible and spring-like so that they will concurrently flexibly and returnably move outwardly as an umbilical catheter 12 is passed through the interior of the funnel-like upper body portion 14 and thus guided into the interior space of the plurality of nibs 16 and out the lower or distal end thereof as shown in FIG. 2. The outwardly movement of the plurality of nibs 16 is indicated by arrows 26 in FIG. 1 and illustrated in the outward position around the end 28 of umbilical catheter 12 in FIG. 2.

It is to be noted that taper of the aforementioned tapered sides of the funnel-like upper body portion 14 continues as a taper of the plurality of nibs 16. As the taper of the plurality of nibs 16 continues to the distal end 24 the outside diameter is extremely small to permit introduction into an umbilical artery as hereinafter described.

Internally, the interior face of the funnel-like upper body portion 14 also tapers in funnel-like configuration, the taper continuing as a taper on the internal face of each of the plurality of nibs 16. As the plurality of nibs 16 are extended outwardly by the insertion of the umbilical catheter 12 into and through, as hereinbefore described, the passageway through the introducer 10 is opened. A partial opening of the plurality of nibs 16 is illustrated in FIG. 3 to indicate the distal end 32 of the tapered passageway 30 through the introducer 10.

At the distal end 24 of the plurality of nibs 16, the external portion of each nib 16 adjacent to the distal end 24 is formed in a bulbous 34 configuration. As will be described hereinafter, the bulbous 34 end of each nib 16 has a distinct novel and unique function of assisting in holding the introducer 10 in place in an umbilical artery during use.

A thin tapered lead tip 52 is added at the distal end 24 below the bulbous end 34, on each nib 16 to facilitate initial insertion into an umbilical artery as hereinafter described.

To assist in handling the introducer 10 during insertion into an umbilical artery and the associated uses made thereof, a handle or holding means 18 is affixed at or near the open end of the funnel-like upper body portion 14. It is to be understood that the omission of the handle or holding means 18 is within the scope and intent of this invention. If the handle or holding means 18 is omitted, the introducer 10 may be held between a thumb and one or more fingers, or held with forceps or other means, such methods of use is also within the scope and intent of this invention.

Turning now to the use of the introducer 10 as compared with the prior art, reference is made to FIGS. 4, 5, 6, and 7.

Figure 5:
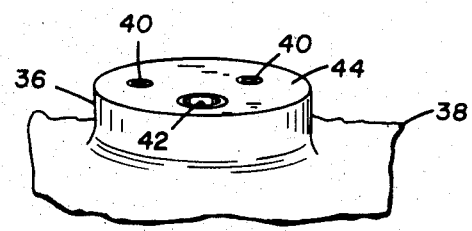
FIG. 5 is a pictorial view of an umbilical stump.

FIG. 5 shows an umbilical stump 36 of an infant after the surgical severance from the umbilical cord. The umbilical stump 36 is shown extending from a portion of an infant's abdomen 38. Inside the umbilical stump 36 can be seen two umbilical arteries 40, an umbilical vein 42, and a jelly-like substance 44, called Wharton's Jelly surrounding the umbilical arteries 40 and the umbilical vein 42.

Figure 6:
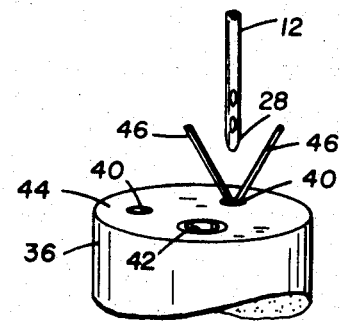
FIG. 6 is a pictorial view of the prior art using forceps and showing a partial view of a catheter about to be inserted in an umbilical artery.
Figure 7:
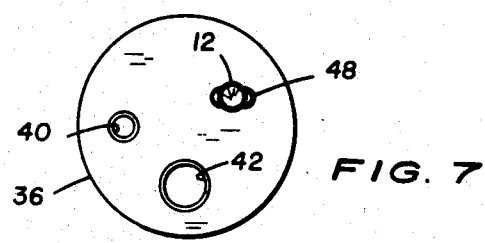
FIG. 7 is a top view of FIG. 6 without the forceps.

In the prior art, shown in FIGS. 6 and 7, forceps 46 are used to pull open the ends or sides of one of the umbilical arteries 40 and hold it open while an umbilical catheter 12 is inserted into the umbilical artery 40. This activity is difficult. Often the tips of the forceps 46 pinch, cut, or tear off a portion of the umbilical artery 40 wall. Also, the pulling open of the end of the umbilical artery 40 by the forceps 46 reforms the entrance to the umbilical artery into an elliptical configuration 48 in relation to the round configuration of the umbilical catheter 12 as shown in FIG. 7.

The forceps 46 that pull the umbilical artery 40 into the elliptical configuration 48 are not shown in FIG. 7 for purposes of clarity. The incompatibility of the round umbilical catheter 12 in relation to the elliptical 48 distortion of the umbilical artery 40 further adds to the difficulty of insertion. Often the end of the umbilical artery 40 is pushed down into the jelly-like substance 44 which is not laterally supportive of the umbilical arteries 40.

When using the introducer 10 of the present invention to insert an umbilical catheter 12 into an umbilical artery 40, the procedure is simplified and positive.

The thin tapered lead tips 52 of the very small bulbous 34 ends of the plurality of nibs 16 are easily slipped into the open end of an umbilical artery 40 and the bulbous ends 34 follow thereafter. If desired or necessary, the umbilical artery may be held and steadied with forceps well below the point where the bulbous 34 ends of the plurality of nibs 16 will be inserted into the selected umbilical artery 40.

Once the introducer 10 is in place the leading end 28 of the umbilical catheter 12 is introduced into the interior passageway 30 of the funnel-like body portion 14 and thence downward to the internal portion of the passageway 30 within the plurality of nibs 16. As the leading end 28 passes downward the plurality of flexible nibs 16 are expanded outwardly and the leading end 28 of the umbilical catheter 12 easily enters the umbilical artery 40. The umbilical catheter 12 may then be inserted to whatever distance the physician requires.

Without the bulbous 34 end the introducer 10 would be exuded from the umbilical artery 40 before the umbilical catheter 12 had been securely inserted into the umbilical artery 40 and thus prevent a successful clinical preparation.

With the bulbous ends 34 inserted into the umbilical artery, the smooth muscle umbilical artery being used first expands and then contracts around both the bulbous 34 ends and the portion of the nibs 16 between the bulbous 34 ends and the funnel-like upper body portion 14.

As the leading end 28 passes through the introducer 10, and the umbilical catheter 12 follows, the plurality of nibs 16 and the bulbous 34 ends are forced outwardly. As this action occurs the smooth muscle of the umbilical artery 40 above the bulbous end 34 contracts further and thus locks the bulbous end 34 into the umbilical artery so that the introducer 10 cannot be exuded from umbilical artery 40. Thus, the problems encountered in the prior art are overcome. The flexible nibs 16 have a memory that maintains their position around the catheter 12.

Once the umbilical catheter 12 is installed, the introducer 10 may be: left in place; pulled from the umbilical artery 40 and slipped, on the catheter cord, away from the infant; or the introducer may be cut and removed from the umbilical catheter.

The introducer 10 may be made from any suitable material. An introducer 10 molded from a suitable plastics is a preferred embodiment.

The umbilical catheter 12 has suitable openings 50 in the end 28 for performing the sampling and monitoring procedures of the blood.

As can be readily understood from the foregoing description of the invention, the present structure can be configured in different modes to provide the ability to introduce an umbilical catheter into an umbilical artery.

Accordingly, modifications and variations to which the invention is susceptible may be practiced without departing from the scope and intent of the appended claims.

What is claimed is:

1. A device for providing a guidance means to insert an object into a very small opening, comprising:
    a body means, said body means being hollow and funnel-like in configuration;
    a plurality of nibs, each nib of said plurality of nibs being very flexible and spring-like, each said nib having a memory, each nib of said plurality of nibs being suitably affixed to said body means;
    a plurality of bulbous means, each bulbous means of said plurality of bulbous means being separately and individually suitably affixed to the distal end of a respective nib of said plurality of nibs opposite to said body means; and
    a plurality of lead tips, said lead tips being very thin and tapered, each thin tapered lead tip of said plurality of lead tips having a wide first end and a narrow second end, said wide first end of each said lead tip being separately and individually suitably affixed to the distal end of a respective bulbous means, said plurality of lead tips serving to guide said plurality of bulbous means into an opening.

2. A guidance device as recited in claim 1, and additionally, a handle means, said handle means being suitably affixed to said body means.

3. A guidance device for guiding an umbilical catheter into an umbilical artery, comprising:
    a body means, said body means being hollow and funnel-like in configuration, said body means having a first end and a second end;
    a plurality of nibs, each nib of said plurality of nibs being very flexible and spring-like, each said nib having a memory, each nib of said plurality of nibs being suitably affixed to said first end of said body means;
    a plurality of bulbous means, each bulbous means of said plurality of bulbous means being separately and individually suitably affixed to the distal end of a respective nib of said plurality of nibs opposite to said body means;

a plurality of lead tips, said lead tips being very thin and tapered, each thin tapered lead tip of said plurality of lead tips having a wide first end and a narrow second end, said wide first end of each said lead tip being separately and individually suitably affixed to the distal end of a respective bulbous means, said plurality of lead tips serving to guide said plurality of bulbous means into an umbilical artery.

4. A guidance device for an umbilical catheter as recited in claim 3 and additionally, a handle means, said handle means being suitably affixed to said second end of said body means.

5. A guidance device for an umbilical catheter as recited in claim 3, wherein said body means with affixed plurality of nibs, bulbous means, and thin tapered lead tips has a passageway therethrough.

6. A guidance means for an umbilical catheter as recited in claim 5, wherein said passageway is tapered.

7. A guidance device for an umbilical catheter as recited in claim 3, wherein said plurality of flexible spring-like nibs are monolithically formed contiguous with said body means.

8. A guidance device for an umbilical catheter as recited in claim 7, wherein said plurality of flexible spring-like nibs are separated by a slit-like opening between each adjacent pair of said nibs.

9. A guidance device for an umbilical catheter as recited in claim 8 and additionally, an inverted teardrop-like opening at the upper portion of each said slit-like opening where said nibs are monolithically and integrally formed contiguous with said body means.

10. A guidance means for an umbilical catheter as recited in claim 3, wherein said plurality of flexible spring-like nibs are formed separately and individually affixed to said body means.

* * * * *